(12) United States Patent
Cimpoia et al.

(10) Patent No.: US 6,541,625 B2
(45) Date of Patent: Apr. 1, 2003

(54) STEREOSELECTIVE SYNTHESIS OF NUCLEOSIDE ANALOGUES

(75) Inventors: Alex Cimpoia, Montreal (CA); Yi Fong Wang, Lexington, MA (US)

(73) Assignee: BioChem Pharma, Inc., Laval (CA)

( * ) Notice: Subject to any disclaimer, the term of this patent is extended or adjusted under 35 U.S.C. 154(b) by 0 days.

(21) Appl. No.: 09/779,853

(22) Filed: Feb. 9, 2001

(65) Prior Publication Data

US 2002/0006635 A1 Jan. 17, 2002

Related U.S. Application Data

(60) Provisional application No. 60/181,977, filed on Feb. 11, 2000.

(51) Int. Cl.⁷ .............. C07H 19/00; C12P 1/00; C12P 41/00
(52) U.S. Cl. .......... 536/27.14; 435/41; 435/87; 435/88; 435/280; 536/22.1
(58) Field of Search ............ 435/41, 87, 88, 435/280; 536/22.1, 27.14, 27.13

(56) References Cited

U.S. PATENT DOCUMENTS

| | | |
|---|---|---|
| 5,283,346 A | 2/1994 | Barner et al. |
| 5,728,575 A | 3/1998 | Liotta et al. |

FOREIGN PATENT DOCUMENTS

| | | |
|---|---|---|
| WO | WO 97/21706 | 6/1997 |
| WO | WO 00/39143 | 7/2000 |
| WO | WO 00/47759 | 8/2000 |

OTHER PUBLICATIONS

Kim et al., L–β–(2S,4S)– and L–α–(2S,4R)–Dioxolanyl Nucleosides as Potential Anti–HIV Agents: Asymmetric Synthesis and Structure—Activity Relationships, Journal of Medicinal Chemistry, Mar. 5, 1993, vol. 36, No. 5, 519–528.

Janes et al., Protease–Mediated Separation of Cis and Trans Diastereomers of 2(R,S)–benzyloxymethyl–4(S)–carboxylic Acid 1,3–Dioxolane Methyl Ester: Intermediates for the Synthesis of Dioxolane Nucleosides, J. Org. Chem, 1999, 64, 9019–9029.

*Primary Examiner*—Samuel Barts
*Assistant Examiner*—Michael C. Henry
(74) *Attorney, Agent, or Firm*—Millen, White, Zelano & Branigan, P.C.

(57) ABSTRACT

The invention is a process for stereoselectively producing a dioxolane nucleoside analogue from an anomeric mixture of β and α anomers represented by the following formula A or formula B:

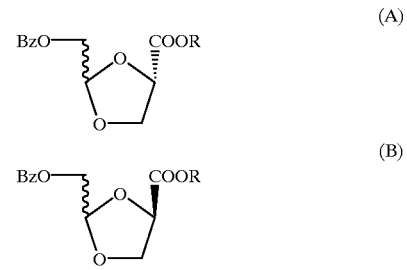

wherein R is selected from the group consisting of $C_{1-6}$ alkyl and $C_{6-15}$ aryl and Bz is benzoyl. The process comprises hydrolyzing said mixture with an enzyme selected from the group consisting of Protease N, Alcalase, Savinase, ChiroCLEC-BL, PS-30, and ChiroCLEC-PC to stereoselectively hydrolyze predominantly one anomer to form a product wherein $R_1$ is replaced with H. The process also includes the step of separating the product from unhydrolyzed starting material. Additionally, the functional group at the C4 position is stereoselectively replaced with a purinyl or pyrimidinyl or derivative thereof.

19 Claims, No Drawings

STEREOSELECTIVE SYNTHESIS OF
NUCLEOSIDE ANALOGUES

This application claims the benefit of U.S. Provisional Application No. 60/181,977, filed Feb. 11, 2000, the entire disclosure of which is hereby incorporated by reference.

FIELD OF THE INVENTION

The present invention relates generally to a novel method for the preparation of nucleoside analogues and their precursors and more particularly to a method of preparing a nucleoside analogue by the use of specific enzymes to stereoselectively produce dioxolane nucleoside analogues or their precursors.

BACKGROUND OF THE INVENTION

An important class of pharmacological agents relate to 3'-oxa-substituted 2',3'-dideoxynucleoside analogues ("dioxolane nucleoside analogues"). These compounds include 9-(β-D-2-hydroxymethyl-1,3-dioxolan-4-yl)-2-aminopurine (β-D-DAPD); 9-(β-D-2-hydroxymethyl-1,3-dioxolan-4-yl)-guanine (β-D-DXG); 1-(β-L-2-hydroxymethyl-1,3-dioxolan-4-yl)-thymine (Dioxolane-T); and 1-(β-L-2-hydroxymethyl-1,3-dioxolan-4-yl)-cytidine (β-L-OddC) which have known antiviral and antitumor activity.

As shown in the following dioxolane structure, dioxolanes have two chiral centers corresponding to the substituted carbons 2 and 4 of the dioxolane ring (C2 and C4 respectively). Thus each compound can exist as four different stereoisomers depending on the position of both substituents with respect to the dioxolane ring.

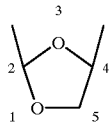

The stereoisomers of a dioxolane nucleoside analogue are represented by the following diagrams where the letter B represents a purine or pyrimidine base or an analogue or derivative of a purine or pyrimidine base as defined herewith.

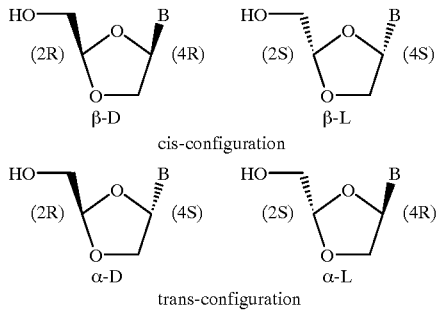

For the purpose of consistency, the same stereochemical designation will be used even when the hydroxymethyl moiety or the base moiety (B) is replaced with another substituent group.

Chiral synthetic methods have improved over the past several years with respect to synthetic techniques that result in single stereoisomer compounds. However, there is a present need to find novel synthetic methods which can be widely used to form a particular stereoisomer with greater efficiency and purity.

For example, for many years a person of ordinary skill in the art could use enzymes to separate enantiomers of dioxolane compounds. However, there is still a need in the art to produce a dioxolane nucleoside analogue using a step of separating an anomeric mixture of certain dioxolane precursors to produce an end product with greater efficiency and purity.

Because stereochemically pure dioxolane nucleosides are an important class of compounds due to their known antiviral activity and anticancer activity, there is a need for other inexpensive and efficient stereoselective methods for their preparation. The present invention satisfies this and other needs.

SUMMARY OF THE INVENTION

The present invention provides a novel process for making dioxolane nucleoside analogues with a high degree of steric purity, greater efficiency and higher yields.

Specifically, the present invention provides a process for making dioxolane nucleoside analogues with a high degree of steric purity which includes the use of certain hydrolytic enzymes for separating β and α anomers from an anomeric mixture represented by the following formula A or formula B:

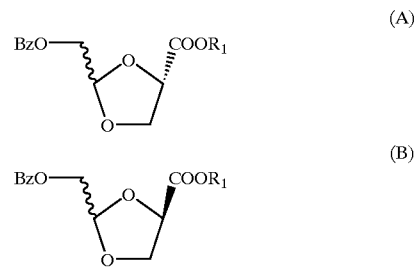

wherein $R_1$ is selected from the group consisting of $C_{1-6}$ alkyl and $C_{6-15}$ aryl; Bz is Benzoyl.

The process involves the step of hydrolyzing the mixture of compounds represented by formula A and/or formula B with an enzyme selected from the group consisting of Protease N (Bacillus subtilus protease), Alcalase® (Subtilisin Carlsberg protease), Savinase® (Bacillus lentus subtilisin protease), ChiroCLEC™-BL (Bacillus licheniformis Subtilisin protease), PS-30 (Pseudomonas cepacia lipase), and ChiroCLEC™-PC (Pseudomonas cepacia lipase). The process stereoselectively hydrolyses predominantly one anomer to form a product where $R_1$ of formula A and formula B is replaced with H. The other anomer remains substantially unhydrolysed. The process also comprises separating the hydrolyzed product from unhydrolysed starting material.

According to one embodiment of the invention, the aforementioned steps of hydrolyzing and separating results in an isolated starting material having an anomeric purity of at least 97% β-anomer. In an additional embodiment, the aforementioned steps of hydrolyzing and separating results in an isolated starting material having an anomeric purity of at least 98% β-anomer. In an additional embodiment, the aforementioned steps of hydrolyzing and separating results in an isolated starting material having an anomeric purity of at least 98.5% β-anomer. In an additional embodiment, the aforementioned steps of hydrolyzing and separating results in an isolated starting material having an anomeric purity of at least 98.8% β-anomer.

According to one embodiment of the invention, the aforementioned steps of hydrolyzing and separating results in an isolated product having an anomeric purity of at least 97% α-anomer. In an additional embodiment, the aforementioned steps of hydrolyzing and separating results in an isolated product having an anomeric purity of at least 98% α-anomer. In an additional embodiment, the aforementioned steps of hydrolyzing and separating results in an isolated product having an anomeric purity of at least 98.5% α-anomer. In an additional embodiment, the aforementioned steps of hydrolyzing and separating results in an isolated product having an anomeric purity of at least 98.8% α-anomer.

In one embodiment, the β-anomer is the predominant product. In another embodiment, the α-anomer is the predominant product. In yet another embodiment, the β-L-enantiomer is the predominant product. In an additional embodiment, the β-D-enantiomer is the predominant product. In yet another embodiment, the α-L-enantiomer is the predominant product. In an additional embodiment, the α-D-enantiomer is the predominant product.

In one embodiment, the invention is a process for stereoselectively preparing a dioxolane nucleoside analogue by separating β and α-nomers from an anomeric mixture represented by formula A or formula B according to one of the above embodiments. The process further includes the step of stereoselectively replacing the functional group at the C4 position (COOR$_1$) with a purinyl or pyrimidinyl or analogue or derivative selected from the group consisting of:

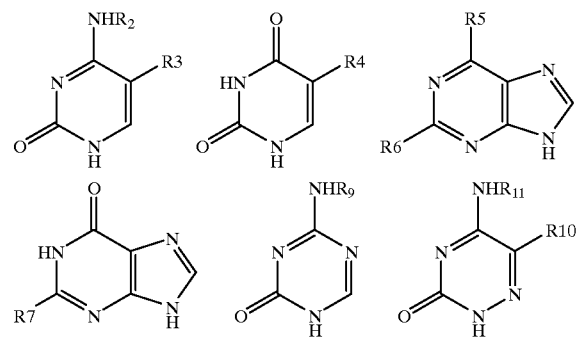

In this embodiment, R$_2$, R$_9$ and R$_{11}$ are independently selected from the group consisting of hydrogen, C$_{1-6}$ alkyl, C$_{1-6}$ acyl and R$_8$C(O) wherein R$_8$ is hydrogen or C$_{1-6}$ alkyl. Additionally, R$_3$, R$_4$ and R$_{10}$ are each independently selected from the group consisting of hydrogen, C$_{1-6}$ alkyl, bromine, chlorine, fluorine, iodine and CF$_3$; and R$_5$, R$_6$ and R$_7$ are each independently selected from the group consisting of hydrogen, bromine, chlorine, fluorine, iodine, amino, hydroxyl and C$_{3-6}$ cycloalkylamino. The process results in the production of a stereochemical isomer of the dioxolane nucleoside analogue.

According to one embodiment, the process further includes the step of stereoselectively replacing the functional group at the C4 position (COOR$_1$) with a purinyl or pyrimidinyl or derivative selected from the group consisting of:

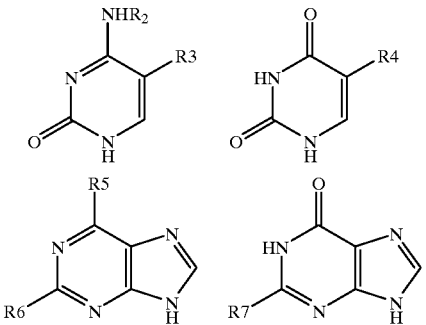

In this embodiment, R$_2$ is selected from the group consisting of hydrogen, C$_{1-6}$ alkyl, C$_{1-6}$ acyl and R$_8$C(O) wherein R$_8$ is hydrogen or C$_{1-6}$ alkyl. Additionally, R$_3$ and R$_4$ are each independently selected from the group consisting of hydrogen, C$_{1-6}$ alkyl, bromine, chlorine, fluorine, iodine and CF$_3$; and R$_5$, R$_6$ and R$_7$ are each independently selected from the group consisting of hydrogen, bromine, chlorine, fluorine, iodine, amino, hydroxyl and C$_{3-6}$ cycloalkylamino. The process results in the production of a stereochemical isomer of a dioxolane nucleoside analogue.

In another embodiment, the process further includes the step of stereoselectively replacing the functional group at the C4 position (COOR$_1$) with a pyrimidinyl or analogue or derivative selected from the group consisting of:

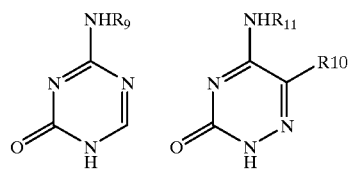

In this embodiment, R$_9$ and R$_{11}$ are independently selected from the group consisting of hydrogen, C$_{1-6}$ alkyl, C$_{1-6}$ acyl and R$_8$C(O). Additionally, R$_{10}$ is selected from the group consisting of hydrogen, C$_{1-6}$ alkyl, bromine, chlorine, fluorine, iodine and CF$_3$. The process results in the production of a stereochemical isomer of a dioxolane nucleoside analogue.

In another embodiment, the process comprises stereoselectively preparing a dioxolane nucleoside analogue by separating β and α anomers from an anomeric mixture represented by formula A or formula B according to one of the above embodiments and further comprises stereoselectively replacing the functional group at the C4 position (COOR$_1$) with a moiety selected from the group consisting of:

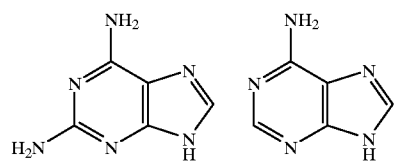

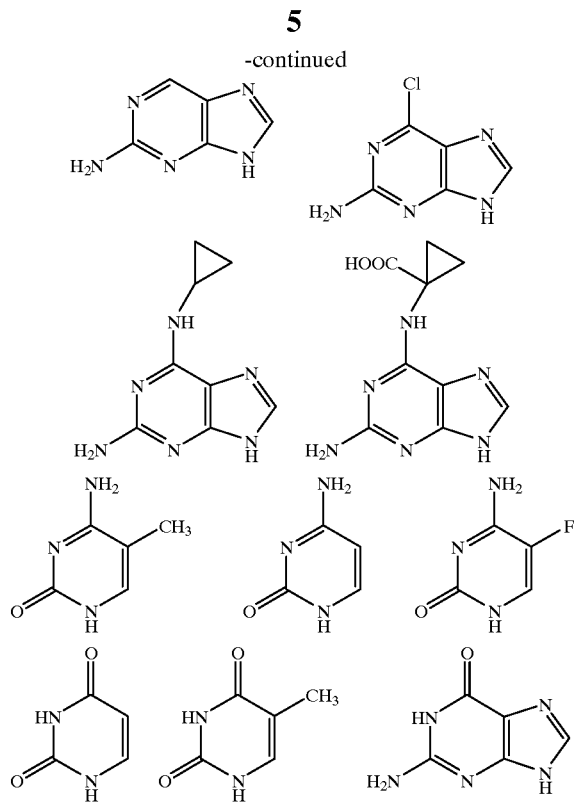

In another embodiment of the present invention, the process comprises making a dioxolane nucleoside analogue by separating a compound according to formula A or formula B. According to this embodiment, the process includes stereoselectively replacing the R group with a 9-purinyl or 1-pyrimidinyl moiety or analogue or derivative thereof by acylating the second mixture to produce an acylated second mixture. This embodiment also includes the step of glycosylating the acetylated second mixture with a purine or pyrimidine base or analogue or derivative thereof and a Lewis Acid to produce a dioxolane nucleoside analogue.

DETAILED DESCRIPTION OF THE INVENTION

The present invention involves a high yield process of separating β and α anomers from an anomeric mixture of dioxolane nucleoside analogue precursors which provides higher yield and greater efficiency. In one embodiment, this method is used in the production of dioxolane nucleoside analogues having a high degree of anomeric purity at lower cost. Additionally, another aspect of the present invention involves synthesizing starting material having a higher degree of anomeric purity.

The present invention provides a process of preparing dioxolane nucleoside analogues having a predominant β-L-configuration using enzymes, namely hydrolases. The procedure improves overall yield and has relatively few steps, thereby improving overall efficiency. The process involves the following steps.

A mixture of anomers represented by formula A or formula B is obtained as described herein in Scheme 1.

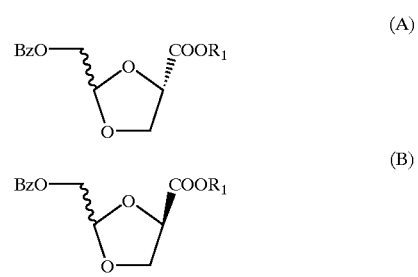

In the above formula, $R_1$ is selected from the group consisting of H, $C_{1-6}$ alkyl and $C_{6-15}$ aryl and Bz is Benzoyl. The mixture is hydrolyzed with an enzyme selected from the group consisting of Alcalase® (Subtilisin Carlsberg protease, Novo Nordisk), Savinase® (Bacillus lentus subtilisin protease, Novo Nordisk), ChiroCLEC™-BL (Bacillus licheniformis Subtilisin protease, Altus Biologics, Inc.), PS-30 (Pseudomonas cepacia lipase, Amano), Protease N (Bacillus subtilus protease, Amano) and ChiroCLEC™-PC (Pseudomonas cepacia lipase, Altus Biologics, Inc.). The hydrolyzing step stereoselectively hydrolyzes the α-anomer of the mixture of either formula A or formula B. The result is an unhydrolyzed β-anomer. The α-anomer can be separated easily from the β-anomer. If an anomeric mixture of the compound of formula A is selected, the result is the production of the compound of formula C and formula D:

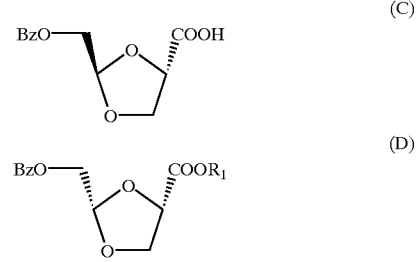

If an anomeric mixture of the compound of formula B is selected, the result is the production of the compound of formula E and formula F:

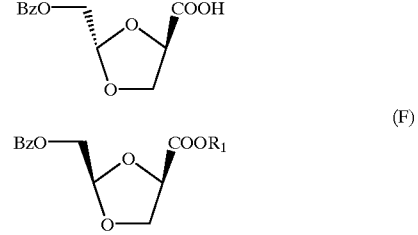

The mixture (C)/(D) or (E)/(F) is then subjected to oxidative decarboxylation which replaces the $R_1$ group with an acyl moiety. It is then glycosylated with a purine or pyrimidine base or analogue or derivative thereof in the presence of a Lewis Acid. The final step produces a dioxolane nucleoside analogue in the β-L configuration for the mixture (C)/(D) and a dioxolane nucleoside analogue in the β-D configuration for the mixture (E)/(F).

At the outset, the following definitions have been provided as reference. Except as specifically stated otherwise, the definitions below shall determine the meaning throughout the specification.

"Nucleoside" is defined as any compound which consists of a purine or pyrimidine base, linked to a pentose sugar.

"Dioxolane nucleoside analogue" is defined as any compound containing a dioxolane ring as defined hereinafter linked to a purine or pyrimidine base or analogue or derivative thereof. A "dioxolane ring" is any substituted or unsubstituted five member monocyclic ring that has an oxygen in the 1 and 3 positions of the ring as illustrated below:

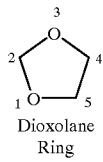

Dioxolane Ring

"Purine or pyrimidine base" is defined as the naturally occurring purine or pyrimidine bases adenine, guanine, cytosine, thymine and uracil. A purine or pyrimidine that is a moiety is a purinyl or pyrimidinyl, respectively.

"Alkyl" is defined as a substituted or unsubstituted, saturated or unsaturated, straight chain, branched chain or carbocyclic moiety, wherein the straight chain, branched chain or carbocyclic moiety can be optionally interrupted by one or more heteroatoms (such as oxygen, nitrogen or sulfur). A substituted alkyl is substituted with a halogen (F, Cl, Br, I), hydroxyl, amino or $C_{6-20}$ aryl.

"Aryl" is defined as a carbocyclic moiety which can be optionally substituted or interrupted by one heteroatom (such as oxygen, nitrogen or sulfur) and containing at least one benzenoid-type ring (such as phenyl and naphthyl).

"Carbocyclic moiety" is defined as a substituted or unsubstituted, saturated or unsaturated, $C_{3-6}$ cycloalkyl wherein a substituted cycloalkyl is substituted with a $C_{1-6}$ alkyl, halogen (i.e. F. Cl, Br, I), amino, carbonyl or $NO_2$.

A "derivative" of a purine or pyrimidine base refers to one of the following structures:

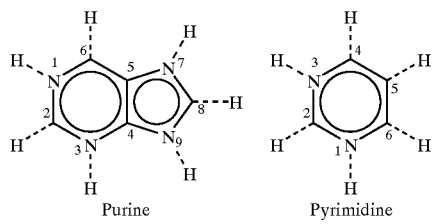

Purine　　　　Pyrimidine wherein one or more of the pyrimidine H are substituted with substituents that are known in the art. In the above illustration, the bonds represented by a broken line are optional and are present only in cases which require the bond to complete the valence of the ring atom. Substitutents bound to the ring members by a single bond include but are not limited to halogen such as F, Cl, Br, I; an akyl such as lower akyls; aryl; cyano carbamoyl; amino including primary, secondary and tertiary amino; and hydroxyl groups. Substituents bound to the carbon ring atoms by a double bond include but are not limited to a =O to form a carbonyl moiety in the ring. It is understood that when the ring is aromatic, some of the substitutions may form tautomers. The definition shall include such tautomers.

"Analogue" of a purine or pyrimidine base refers to any derivative of purine or pyrimidine bases that is further modified by substituting one or more carbon in the ring structure with a nitrogen.

"Stereoselective enzymes" are defined as enzymes which participate as catalysts in reactions that selectively yield one specific stereoisomer over other stereoisomers.

"Anomeric purity" is defined as the amount of a particular anomer of a compound divided by the total amount of all anomers of that compound present in the mixture multiplied by 100%.

"Alkoxy" is defined as an alkyl group, wherein the alkyl group is covalently bonded to an adjacent element through an oxygen atom (such as methoxy and ethoxy).

"Alkoxycarbonyl", is defined as an alkoxy group attached to the adjacent group of a carbonyl.

"Acyl" is defined as a radical derived from a carboxylic acid, substituted (by a halogen, $C_{6-20}$ aryl or $C_{1-6}$ alkyl) or unsubstituted by replacement of the —OH group. Like the acid to which it is related, an acyl radical may be aliphatic or aromatic, substituted (by halogen, $C_{1-6}$ alkoxyalkyl, nitro or $O_2$) or unsubstituted, and whatever the structure of the rest of the molecule may be, the properties of the functional group remain essentially the same (such as acetyl, propionyl, isobutanoyl, pivaloyl, hexanoyl, trifluoroacetyl, chloroacetyl and cyclohexanoyl).

"Alkoxyalkyl" is defined as an alkoxy group attached to the adjacent group by an alkyl group (such as methoxymethyl).

"Acyloxy" is defined as an acyl group attached to the adjacent group by an oxygen atom.

"Oxo" is defined as a =O substituent bonded to a carbon atom.

"Hydroxy protecting group" is well known in the field of organic chemistry. Such protecting groups may be found in T. Greene, Protective Groups in Organic Synthesis, (John Wiley & Sons, 1981). Examples of hydroxy protecting groups include but are not limited to benzyl, benzoyl, substituted benzoyl, acetyl and substituted acetyl.

As noted above, one embodiment of the present invention is a process for separating β and α anomers from an anomeric mixture represented by the following formula A or formula B:

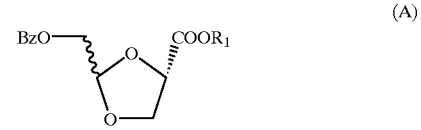

(A)

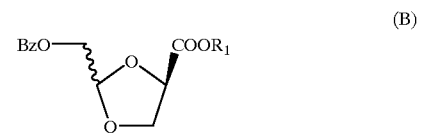

(B)

wherein $R_1$ is selected from the group consisting of $C_{1-6}$ alkyl and $C_{6-15}$ aryl; Bz is Benzoyl.

Another embodiment of the present invention is a process for separating β and α anomers from an anomeric mixture represented by the following formula A' or formula B':

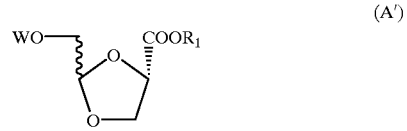

(A')

-continued

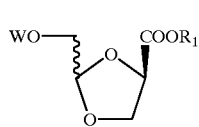
(B')

wherein $R_1$ is selected from the group consisting of $C_{1-6}$ alkyl and $C_{6-15}$ aryl; W is a hydroxy protecting group.

In one embodiment, the process stereoselectively hydrolyses predominantly the α-anomer to form a product where $R_1$ of formula A and formula B is replaced with H. The β-anomer remains substantially unhydrolyzed. The process also comprises separating the hydrolyzed product from unhydrolyzed starting material.

The process of making a β-L dioxolane nucleoside analogue begins with the preparation of starting materials. Scheme 1 depicts the manufacture of a mixture that includes formula A or B.

Scheme 1

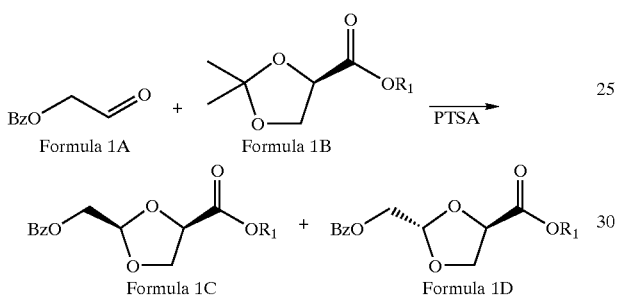

A benzoyloxyacetaldehyde (formula 1A) is reacted with 1,3-dioxolane-4-carboxylic acid-2,2-dimethyl-methyl ester (formula 1B) in approximately equimolar proportions. The dioxolane of formula 1B has a chiral center at the C4 carbon. The reaction occurs in a toluene solvent. The mixture is heated to 58° C. The catalyst, PTSA, is added. The mixture is heated to a temperature between 64–67° C. A vacuum is applied at 70 kPa, and the reaction proceeds for 40 minutes. Traces of solvent are then removed by high vacuum. The catalyst is removed by filtration using a 1:1 ratio of Hexane:EtOAc as an eluent. In one embodiment, the preferred filter is a silica gel pad. The resulting product is a crude oil containing a mixture of the compounds of formula 1C and 1D wherein the ratio is 2:1 of (1C:1D), respectively.

It can be appreciated by a person of skill in the art that the reaction conditions can be adjusted to optimize the purity of the stereoisomers. In one embodiment of the present invention, the reaction of the compound of formula 1A with the compound of formula 1B is done in the presence of catalyst in an amount between about 1.0 wt % and 10.0 wt % of the starting material. In another embodiment the amount of catalyst is between about 2.5 wt % and about 5.5 wt % of the starting materials. In yet another embodiment, the amount of catalyst is between about 3.0 wt % and about 5.0 wt %. In still another embodiment, the amount of catalyst is between about 3.5%. and about 5.5%. In another embodiment, the amount of catalyst is between about 2.5 wt % and about 7.5 wt %. In another embodiment the amount of catalyst is about 5.0 wt %.

In an embodiment of the present invention, the reaction of the compound of formula 1A with the compound of formula 1B is done at a temperature ranging from about 40° C. to about 80° C. In another embodiment of the present invention, the temperature ranges from about 50° C. to about 75° C. In still another embodiment, the temperature ranges from about 60° C. to about 70° C. In an additional embodiment, the temperature ranges from about 65° C. to about 79° C.

In an embodiment of the present invention, the reaction time between the compound of formula 1A and the compound of formula 1B corresponds to a period ranging from about 30 minutes to about 2 hours. In yet another embodiment, the period ranges from about 30 minutes to about 1 hour. In still another embodiment, the period ranges from about 30 minutes to about 50 minutes.

It will be appreciated by a person of ordinary skill in the art that the C4 carbon is chiral. Because this carbon is not involved in the reaction, the chirality is preserved at that carbon. A starting material can be selected to have a (4S) or (4R) stereochemistry.

According to one embodiment, it is preferable that the resulting product is an anomeric mixture favoring the β-L configuration over the α-L configuration. To achieve such a result, the starting material represented by formula 1B (4S) is selected and shown below:

Formula 1B (4S)

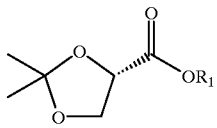

The reaction proceeds according to the principles described above. The resulting product, according to one embodiment, will have an anomeric purity of the β-L anomer over the α-L anomer of greater than 55%, preferably 60% and more preferably 65%.

According to one embodiment, the present invention is a method of separating β-anomers from α-anomers according to the following Scheme 2:

Scheme 2

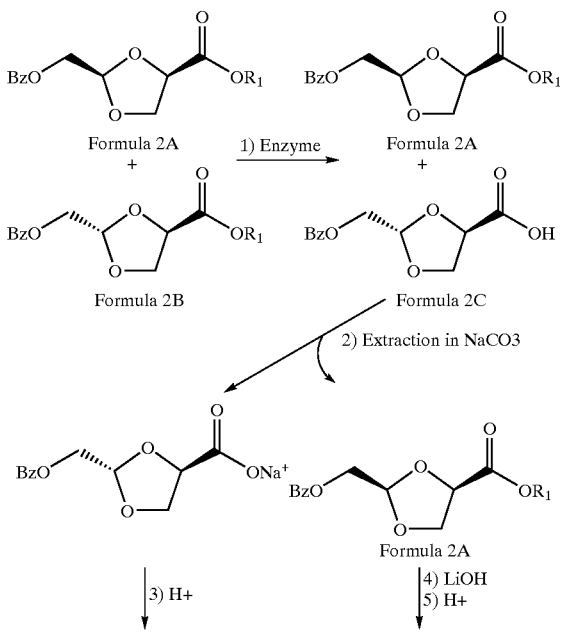

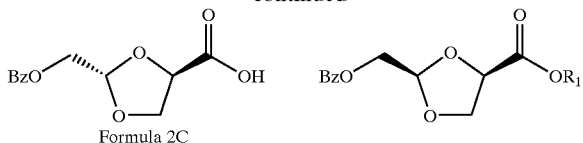

Formula 2C

According to one embodiment, a mixture of anomers is obtained as represented by formula 2A or formula 2B. A mixture represented by formula 2A or formula 2B can be obtained according to the reaction described above or according to any method known in the art.

The reaction is prepared as follows: A portion of the material containing a mixture of compounds represented by formula 2A and formula 2B is weighed into a reaction vessel. According to one embodiment, about 3.7% mmol of the mixture is added to 10 mL of 20% acetonitrile/aqueous buffer. In another embodiment for a preparative scale reaction, about 75.2 mmole of the mixture is added to about 200 ml of 20% acetonitrile/aqueous buffer. The buffer is a phosphate buffer with a pH between 7.0 and 7.5 and preferably 7.2. In another embodiment a 20% aqueous t-butyl methyl ether was used.

The enzyme is selected from the group consisting of Alcalase® (Subtilisin Carlsberg protease), Savinase® (Bacillus lentus subtilisin protease), ChiroCLEC™-BL (Bacillus licheniformis Subtilisin protease), PS-30 (Pseudomonas cepacia lipase), Protease N (Bacillus subtilus protease), and ChiroCLEC™-PC (Pseudomonas cepacia lipase). These enzymes are commercially available. Particularly, some of the materials can be obtained from the following sources: Savinase® and Alcalase® can be obtained from Novo Nordisk. ChiroCLEC™-BL and ChiroCLEC™ can be obtained from Altus Biologics, Inc. PS-30 and Protease N can be obtained from Amano Pharmaceutical.

The stereospecific enzyme selected is then added to begin the hydrolysis reaction. The enzymatic reaction hydrolyzes primarily the α-anomer by replacing the $R_1$ group of the α-anomer of the compound of formula 2B with H to form the compound of formula 2C. The amount of the enzyme added can be determined according to principles known by any person of ordinary skill in the art. According to another embodiment, about 500 mL was added to begin the reaction. The rate and degree of hydrolysis was monitored by a pH-stat according to principles known in the art. As the compound of formula 2B is hydrolyzed, the pH of the mixture decreases. Thus, the change in pH as monitored by a pH-stat corresponds to the completeness of the reaction.

If the reaction time is allowed to proceed longer than the optimal reaction time, the β-anomer may be converted resulting in lower chemical yield of the final product. If the reaction time is too short, less than optimal amount of the α-anomer is converted resulting in a lower anomeric purity of the remaining unhydrolyzed reactant. According to one embodiment, the reaction is allowed to proceed until 43% completion. It will be appreciated by a person of ordinary skill in the art that the exact degree of completion may change depending upon the reactant used, the enzyme used and other principles known to a person of ordinary skill in the art.

As noted, the ester starting material and the hydrolysed product are separated by increasing the pH of the solution to more than pH 7.0 and in one embodiment below pH 7.5 with sodium bicarbonate and extracting with ethyl acetate (for example, 3×80 mL). The unhydrolysed starting material is extracted in the ethyl acetate and the hydrolysed product remains in salt form in the aqueous solution. The pH of the solution is then adjusted to pH 2. The hydrolyzed product is further extracted with ethyl acetate (for example, 3×80 mL). The reactants and the products are dried with $MgSO_4$, filtered and concentrated in-vacuo.

Additionally, the unhydrolysed product can be hydrolysed by procedures known in the art such as reaction with LiOH followed by acidification.

Because of the enzyme selectivity, the anomeric purity of the hydrolyzed and separated α-anomer is considerably high.

According to one embodiment of the invention, the aforementioned steps of hydrolyzing and separating results in an isolated starting material having an anomeric purity of at least 97% β-anomer. In an additional embodiment, the aforementioned steps of hydrolyzing and separating results in an isolated starting material having an anomeric purity of at least 98% β-anomer. In an additional embodiment, the aforementioned steps of hydrolyzing and separating results in an isolated starting material having an anomeric purity of at least 98.5% β-anomer. In an additional embodiment, the aforementioned steps of hydrolyzing and separating results in an isolated starting material having an anomeric purity of at least 98.8% β-anomer.

According to one embodiment of the invention, the aforementioned steps of hydrolyzing and separating results in an isolated product having an anomeric purity of at least 97% α-anomer. In an additional embodiment, the aforementioned steps of hydrolyzing and separating results in an isolated product having an anomeric purity of at least 98% α-anomer. In an additional embodiment, the aforementioned steps of hydrolyzing and separating results in an isolated product having an anomeric purity of at least 98.5% α-anomer. In an additional embodiment, the aforementioned steps of hydrolyzing and separating results in an isolated product having an anomeric purity of at least 98.8% α-anomer.

In another embodiment, the procedure of Scheme 2 is followed except the anomeric mixture represented by formula 2A and 2B is replaced with an anomeric mixture represented by formula 2D and 2E, respectively.

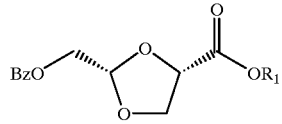

Formula 2D

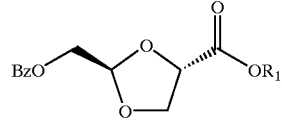

Formula 2E

According to this embodiment the α-anomer represented by formula 2E is hydrolyzed. The result is the separation of the hydrolyzed α-anomer represented by formula 2F from the unhydrolyzed β-anomer represented by formula 2D.

Formula 2F

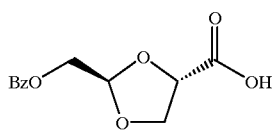

In another embodiment, the procedure of Scheme 2 is followed except a mixture represented by formula 2A and 2B is replaced with a mixture of four stereoisomers represented by formula 2G.

Formula 2G

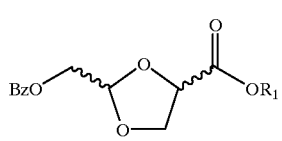

According to this embodiment, the α-anomer containing both D and L enantiomers is hydrolyzed. The result is the separation of the hydrolyzed α-anomer containing both D and L enantiomers from the unhydrolyzed β-anomer containing both D and L enantiomers.

After hydrolysis, purification and oxidative decarboxylation, the resulting dioxolane ring can be linked with a purine or pyrimidine base or analogue or derivative. There are several examples known by skilled artisan on how to link a purine or pyrimidine base or analogue or derivative to the dioxolane ring. For example, PCT Publ. No. WO/97/21706 by Mansour et al. describes one method of stereoselectively attaching the purine or pyrimidine base or analogue or derivative to a dioxolane ring. WO/97/21706 is incorporated herein fully by reference.

According to the process disclosed in WO/97/21706 the starting material is an acylated dioxolane ring. The starting material of the procedure disclosed in WO/97/21706 can be obtained by oxidative decarboxylation of a product of Scheme 2 discussed above. Oxidative decarboxylation destroys the stereochemistry of the C4 carbon while preserving the stereochemistry of the C2 carbon.

As noted, the oxidative decarboxylation step occurs after the hydrolysis step of Scheme 2. A compound having the desired stereochemistry on the C2 carbon is selected. For each mmol of compound that is processed, it is dissolved in between about 2.5 and about 4.0 mL of acetonitrile. In another embodiment, between about 3.0 and about 3.5 mL of acetonitrile was added for each mmol of compound. In yet another embodiment, between about 3.3 and about 3.4 mL of acetonitrile was added for each mmol of compound.

For each mmol of compound, between about 0.08 and about 0.12 mL of pyridine was added. In another embodiment, between about 0.09 and about 0.11 mL of pyridine was added for each mmol of compound. In yet another embodiment, approximately 0.1 mL of pyridine was added for each mmol of compound.

To this mixture, between 1.1 and 1.5 mmoles of Pb(OAc)$_4$ was added for each mmol of compound. In another embodiment, between about 1.2 mmoles and about 1.4 mmoles of Pb(OAc)$_4$ is added for each mmol of compound. In yet another embodiment, about 1.3 mmoles of Pb(OAc)$_4$ is added for each mmol of compound.

Thereafter, the mixture was stirred for 18 hours at room temperature. Then, the mixture was poured into a saturated solution of NaHCO$_3$. Between approximately 2.0 and 3.0 mL of NaHCO$_3$ were used for each mmol of compound. In one embodiment, between about 2.5 mL and about 2.7 mL, and more preferably about 2.6 mL of NaHCO$_3$ was used for each mmol of compound. The solution was then stirred for an additional 30 minutes. The organic layer was separated from the aqueous layer by four extractions of ethyl acetate. Extracts were combined, dried on anhydrous Na$_2$SO$_4$ and evaporated under a vacuum. Optionally, the crude can be further purified by chromatography on silica gel using a gradient of 0–15% ethyl acetate in hexane.

In one embodiment of the present invention, the oxidative decarboxylation step is followed by glycosylation. The glycosylation is represented by the following Scheme 3.

SCHEME 3

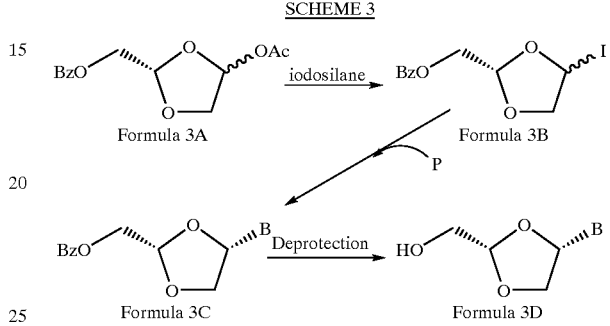

The first step in the glycosylation procedure is to obtain a compound with the desired stereospecificity at the C2 carbon. According to one embodiment, a compound having an S stereochemistry at the C2 carbon, as represented by the compound of formula 3A is preferred. The result is that a higher ratio of the β-L anomer is in the product 3C. According to another embodiment, a compound having an R stereochemistry at the C2 carbon is preferred. The result is a product that has a higher ratio of the β-D anomer in the final product.

The compound of formula 3A is reacted with an iodosilane to produce the compound of formula 3B. In one embodiment, the iodosilane is iodotrimethylsilane.

In another embodiment, the iodosilane is diiodosilane. Important to the reaction is that it occurs at low temperatures. According to one embodiment, the temperature is preferably between 0° C. and −78° C. prior to glycosylation with silylated pyrimidine or purine base or analogue or derivative thereof. According to another embodiment, the temperature is between 0° C. and −14.9° C. prior to glycosylation with silylated pyrimidine or purine base or analogue or derivative thereof. According to yet another embodiment, the temperature is between 0° C. and −78° C. prior to glycosylation with silylated purine base or analogue or derivative selected from the group comprising:

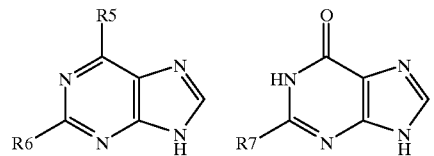

wherein R$_5$, R$_6$ and R$_7$ are each independently selected from the group consisting of hydrogen, bromine, chlorine, fluorine, iodine, amino, hydroxyl and C$_{3-6}$ cycloalkylamino.

According to still another embodiment, the temperature is between 0° C. and −78° C. prior to glycosylation with silylated purine base or analogue or derivative thereof selected from the group comprising:

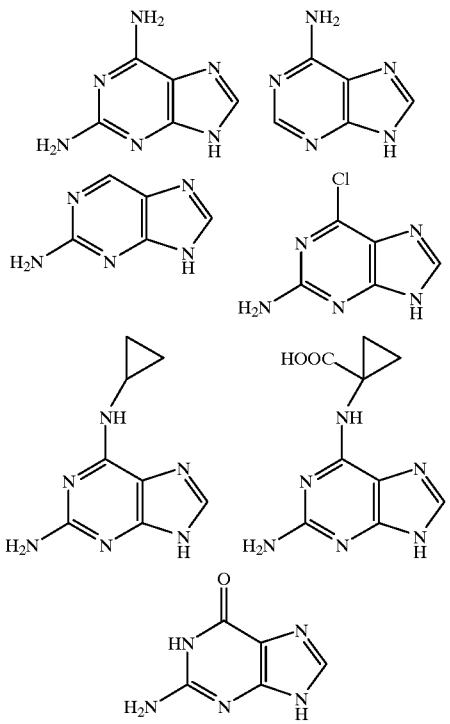

The iodo intermediate represented by formula 3B is then dissolved in dichloromethane and is cooled down to a temperature comparable to the temperature of the reaction vessel.

A purine or pyrimidine base or analogue or derivative thereof is then selected. According to one embodiment, the purine or pyrimidine base or analogue or derivative thereof is selected from the following group:

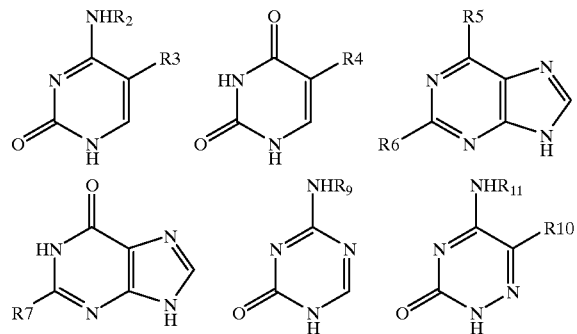

wherein $R_2$, $R_9$ and $R_{11}$ are each independently selected from the group consisting of hydrogen, $C_{1-6}$ alkyl, $C_{1-6}$ acyl and $R_8C(O)$ wherein $R_8$ is hydrogen or $C_{1-6}$ alkyl;

$R_3$, $R_4$ and $R_{10}$ are each independently selected from the group consisting of hydrogen, $C_{1-6}$ alkyl, bromine, chlorine, fluorine, iodine and $CF_3$; and $R_5$, $R_6$ and $R_7$ are each independently selected from the group consisting of hydrogen, bromine, chlorine, fluorine, iodine, amino, hydroxyl and $C_{3-6}$ cycloalkylamino.

According to one embodiment, the purine or pyrimidine base or derivative is selected from the group consisting of:

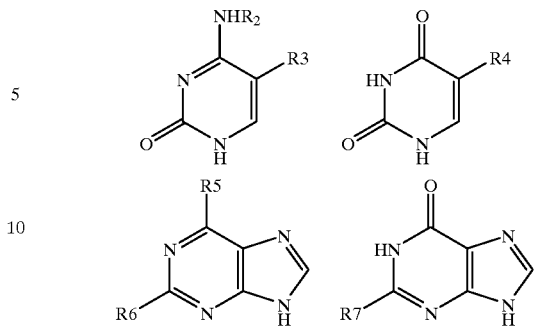

In this embodiment, $R_2$ is selected from the group consisting of hydrogen, $C_{1-6}$ alkyl, $C_{1-6}$ acyl and $R_8C(O)$ wherein $R_8$ is hydrogen or $C_{1-6}$ alkyl. Additionally, $R_3$ and $R_4$ are each independently selected from the group consisting of hydrogen, $C_{1-6}$ alkyl, bromine, chlorine, fluorine, iodine and $CF_3$; and $R_5$, $R_6$ and $R_7$ are each independently selected from the group consisting of hydrogen, bromine, chlorine, fluorine, iodine, amino, hydroxyl and $C_{3-6}$ cycloalkylamino.

In another embodiment, the purine or pyrimidine base or analogue or derivative thereof is selected from the group consisting of:

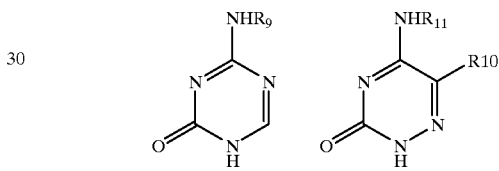

In this embodiment, $R_9$ and $R_{11}$ are independently selected from the group consisting of hydrogen, $C_{1-6}$ alkyl, $C_{1-6}$ acyl and $R_8C(O)$. Additionally, $R_{10}$ is selected from the group consisting of hydrogen, $C_{1-6}$ alkyl, bromine, chlorine, fluorine, iodine and $CF_3$.

The purine or pyrimidine or analogue or derivative thereof is persylated by a sylating agent and ammonium sulphate followed by evaporation of HMDS to form a persylated purine or pyrimidine base or analogue or derivative thereof herein referred to as the persylated base and designated as P in Scheme 3. According to one embodiment, the sylating agent is selected from the group consisting of 1,1,1,3,3,3-hexamethyldisilazane, trimethylsilyl triflate, t-butyldimethylsilyl triflate or trimethylsilyl chloride. In one embodiment, the sylating agent is 1,1,1,3,3,3,-hexamethyldisilazane.

The persylated base P was dissolved in 30 mL of dichloromethane and was added to the iodo intermediate represented by formula 3B. The reaction mixture was maintained at between 0 and 78° C. for 1.5 hours then poured onto aqueous sodium bicarbonate and extracted with dichloromethane (2×25 mL). The organic phase was dried over sodium sulphate to obtain the compound of formula 3C. As used in Scheme 3, the B represents a moiety of the purine or pyrimidine base or analogue or derivative thereof which was persylated in the above step to form P. The compound of formula 3C was removed by filtration and the solvent was evaporated in-vacuo to produce a crude mixture. The product represented by formula 3C has predominantly a 4S configuration at the C4 carbon with an anomeric purity of 80%. When the starting material is a compound represented by formula 3A, the product forms predominantly the β-L enantiomer having an anomeric purity of 80%.

Next, the compound of formula 3C is deprotected to produce the compound of formula 3D. This can be accomplished by dissolving a compound represented by formula 3C in methanol and then adding ammonia or sodium methoxide. The deprotection step can also be done by other methods which are well known by those skilled in the art. The product represented by formula 3D is purified by flash chromatography on silica-gel (5% MEOH in ethylacetate). The deprotection step can also be done by other methods that are well known by a person skilled in the art.

In another embodiment, compounds of Scheme 1 may be prepared by an alternative process which is shown below in Scheme 4.

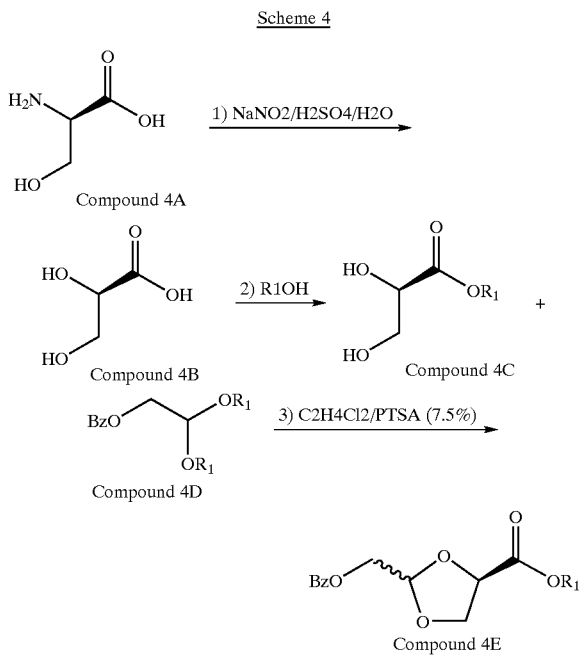

Scheme 4

Compound 4A
Compound 4B
Compound 4C
Compound 4D
Compound 4E

Between about 1.0–1.4 eq of sulfuric acid was added in portions to a large excess of water while stirred at a temperature between 0–5° C. By way of example and not by limitation, if 9.06 mol of D-Serine represents 1 equivalent of reactant, then between about 9.5–13.3 mol of sulfuric acid is added to 7.3 L of water. In another embodiment, between about 1.1–1.3 eq of sulfuric acid was added to an excess of water. In a further embodiment, 1.2 eq of sulfuric acid was added to an excess of water.

About 1 equivalent of D-Serine was added in one portion under vigorous stirring. Then, between about 1.0 and 1.4 eq. of aqueous sodium nitrite was added dropwise. The temperature was kept between 0–5° C. during the addition time (about seven hours). The reaction vessel was stirred overnight at room temperature. The water was removed by vacuum and the residue (D-glyceric acid) co-evaporated with toluene (3×1L). The residue was then stirred with about 6L of an alcohol solvent for about 30 minutes. According to one embodiment, the alcohol is of the formula $R_1OH$ wherein $R_1$ is a $C_{1-4}$ alkyl. According to another embodiment, the alcohol is methanol or ethanol. The resulting solid was removed by filtration. The clear solution was stirred at room temperature for 30–40 hours, the alcohol removed by vacuum to yield a D-glycerate in the form of a yellow viscous syrup. The D-glycerate is then reacted with between about 0.9–1.1 eq of a dialkyl acetal at a temperature of about 85–95° C. Examples of suitable dialkyl acetals include benzoyloxyacetaldehyde dialkyl. Examples of suitable alkyls for the dialkyl acetal is methyl and ethyl.

Then, between about 1 wt % and about 10 wt % of PTSA is added. According to another embodiment, about 5 wt % PTSA is added. In another embodiment, about 0.02 eq. of solid PTSA is added. The reaction mixture is kept under vacuum at a temperature between 85–95° C. for 2–3 hours. The mixture is then cooled to room temperature, diluted with ethylacetate (250 mL) and poured onto saturated sodium bicarbonate solution (250 mL) under stirring. The organic phase is separated and the aqueous phase concentrated, purified on a silica gel column eluting with 5–10% ethylacetate/hexanes to yield the desired dioxolane as a light yellow oil (about 59%) with β/α ratio of 2:1 or higher.

Alternatively, the reactants of step 3 of Scheme 4 can be substituted by corresponding reactants of Scheme 1. For example, the D-glycerate represented by Formula 4C is replaced with an 1,3 dioxolane-4-(4R)carboxylic acid-2,2-dimethyl alkyl ester represented by Formula 1B according to one embodiment. Additionally or alternatively, the dialkyl acetal represented by Formula 4D is replaced with a benzoyloxyaldehyde represented by Formula 1A. These substitutions do not require changing the reaction conditions substantially disclosed above for the third step of Scheme 4.

In a further embodiment of the present invention, the starting material of Scheme 4 is L-Serine which produces an end product having an S-configuration at the C4 carbon of the dioxolane ring. Alternatively, the L-glycerate of Step 3 can be replaced with an 1,3 dioxolane-4-(4S)carboxylic acid-2,2-dimethyl alkyl ester to produce an end product having predominantly an S-configuration at the C4 carbon of the resulting dioxolane ring.

EXAMPLE 1

Enzyme catalyzed hydrolytic resolution of the dioxolane methyl ester using Savinase®

A 2:1 (β:α) anomeric mixture of (2-(S)-benzoyloxymethyl)-4-carboxylic acid-1,3-dioxolane methyl ester) (20 g, 75.2 mmol) was weighed into a reaction vessel and was disolves with 40 mL of acetonitrile. 160 mL of pH 7.2 phosphate buffer was added to form a suspension. Savinase® (5 mL was added to begin the reaction and the rate and degree of hydrolysis was monitored by HPLC analysis with ChiraCel OD column or a pH-stat which maintained the pH at 7 by automatic titration with 1 M NaOH. The reaction was terminated when the anomeric purity of the remaining ester reached 98% (about 8 hours). After the pH of the reaction mixture was adjusted to pH 7.5 with 1 M NaOH, the remaining starting material ester was extracted with ethyl acetate (3×80 mL). The aqueous phase was adjusted to pH 6.0 and the product acid was extracted.

Both extracts were dried with $MgSO_4$, filtered and concentrated in-vacuo. By this method, we obtained the (2-(S)-benzoyloxymethyl)-4-(S)-carboxylic acid-1,3-diaxolanemethyl ester) with greater than 98% anomeric purity.

EXAMPLE 2

Purity of β-Anomer by NMR

Analysis was performed on a Varian Gemini 200 MHz NMR spectrometer in $CDCl_3$. The α-ester shows a triplet at 5.33 ($^3J=4.6$ Hz) and the β-ester shows a triplet upfield at 5.23 ($^3J=4.6$ Hz). The α-acid shows a triplet at 5.33($^3J=3.6$ Hz), while the β-acid shows a broad singlet upfield at d 5.19. We did not observe any epimerization of the substrate or product acid during work-up. By NMR analysis, the purity of the β-anomer is determined to have 98% anomeric purity.

EXAMPLE 3

Purity of the α-Anomer

The product acid is obtained from Example 1 after it was dried with $MgSO_4$, filtered and concentrated in-vacuo. It is analyzed for purity by NMR. The α-anomer is isolated with high anomeric purity.

EXAMPLE 4

Enzymatic Resolution of β-anomer with Alcalase®

The procedures of Examples 1–2 were followed using Alcalase® as the enzyme to separate a 2:1 (β:α) anomeric mixture of (2-(S)-benzoyloxymethyl)-4-carboxylic acid-1,3-dioxolane methyl ester). The result is a β-anomer that has high anomeric purity.

EXAMPLE 5

Enzymatic Resolution of α-anomer Alcalase®

The product acid is obtained from Example 4 after it is dried with $MgSO_4$, filtered and concentrated in-vacuo. The α-anomer is isolated with high anomeric purity.

EXAMPLE 6

Enzymatic Resolution of β-anomer with ChiroCLEC™-BL

The procedures of Examples 1–2 were followed using ChiroCLEC™-BL as the enzyme to separate a 2:1 (β:α) anomeric mixture of (2-(S)-benzoyloxymethyl)-4-carboxylic acid-1,3-dioxalane methyl ester). The result is a β-anomer that has high anomeric purity.

EXAMPLE 7

Enzymatic Resolution of α-anomer with ChiroCLEC™-BL

The product acid is obtained from Example 6 after it is dried with $MgSO_4$, filtered and concentrated in-vacuo. The α-anomer is isolated with high anomeric purity.

EXAMPLE 8

Enzymatic Resolution of β-anomer with PS-30

The procedures of Examples 1–2 were followed using PS-30 as the enzyme to separate a 2:1 (β:α) anomeric mixture of (2-(S)-benzoyloxymethyl)-4-carboxylic acid-1,3-dioxolane methyl ester). The result is a β-anomer that has high anomeric purity.

EXAMPLE 9

Enzymatic Resolution of α-anomer with PS-30

The product acid is obtained from Example 8 after it is dried with $MgSO_4$, filtered and concentrated in-vacuo. The α-anomer is isolated with high anomeric purity.

EXAMPLE 10

Enzymatic Resolution of β-anomer with ChiroCLEC™-PC

The procedures of Examples 1–2 were followed using ChiroCLEC™-PC as the enzyme to separate a 2:1 (β:α) anomeric mixture of (2-(S)-benzoyloxymethyl)-4-carboxylic acid-1,3-dioxolane methyl ester). The result is a β-anomer that has high anomeric purity.

EXAMPLE 11

Enzymatic Resolution of α-anomer with ChiroCLEC™-PC

The product acid is obtained from Example 10 after it is dried with $MgSO_4$, filtered and concentrated in-vacuo. The α-anomer is isolated with high anomeric purity.

EXAMPLE 12

Enzymatic Resolution of β-anomer with Protease N

The procedures of Examples 1–2 were followed using Protease N as the enzyme to separate a 2:1 (β:α) anomeric mixture of (2-(S)-benzoyloxymethyl)-4-carboxylic acid-1,3-dioxolane methyl ester). The result is a β-anomer that has high anomeric purity.

EXAMPLE 13

Enzymatic Resolution of α-anomer with Protease N

The product acid is obtained from Example 12 after it is dried with $MgSO_4$, filtered and concentrated in-vacuo. The α-anomer is isolated with high anomeric purity.

EXAMPLE 14

Preparation of 2-(S)-Benzoyloxymethyl-4-(R)-iodo-1,3-dioxolane and 2-(S)-Benzoyloxymethyl-4-(S)-iodo-1,3-dioxolane (Compound 14)

Compound 14

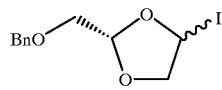

A mixture consisting of 2S-benzoyloxymethyl-4S acetoxy-1,3-dioxolane and 2S-benzoyloxymethyl-4R-acetoxy-1,3-dioxolane in 1:2 ratio (6g; 23.8 mMol) was dried by azeotropic distillation with toluene in-vacuo. After removal of toluene, the residual oil was dissolved in dry dichloromethane (60 mL) and iodotrimethylsilane (3.55 mL; 1.05 eq.) was added at −78° C., under vigorous stirring. The dry-ice/acetone bath was removed after addition and the mixture was allowed to warm up to room temperature (15 min.). The product was 2S-benzoyloxymethyl-4R-iodo-1,3-dioxolane and 2S-benzoyloxymethyl-4S -iodo-1,3-dioxolane.

It would be understood by a person of ordinary skill in the art that if the starting mixture was chosen consisting of 2R-benzoyloxymethyl-4S acetoxy-1,3-dioxolane and 2R-benzoyloxymethyl-4R-acetoxy-1,3-dioxolane. The resulting product is 2R-benzoyloxymethyl-4R-iodo-1,3-dioxolane and 2R-benzoyloxymethyl-4S-iodo-1,3-dioxolane. Furthermore, the starting material having a benzoyl substituent group instead of a benzyl would result in a product having a benzoyl substituent and not a benzyl.

EXAMPLE 15

Synthesis of 2-(S)-Benzoyloxymethyl-1,3-dioxolan-4-(S)-yl)-2-oxo-4-aminoacetyl-pyrimidine (Compound 15)

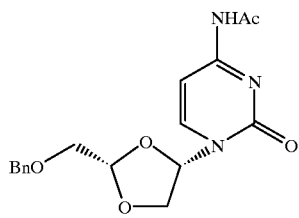

Compound 15

The previously prepared iodo intermediate (Compound 14) in dichloromethane, was cooled down to −78° C. Persylated N-acetyl cytosine (1.1 eq) formed by reflux in 1,1,1,3,3,3-hexamethyl disilazane (HMDS) and ammonium sulphate followed by evaporation of HMDS was dissolved in 30 mL of dichloromethane and was added to the iodo intermediate. The reaction mixture was maintained at −78° C. for 1.5 hours then poured onto aqueous sodium bicarbonate and extracted with dichloromethane (2×25mL). The organic phase was dried over sodium sulphate, the solid was removed by filtration and the solvent was evaporated $_{in\text{-}vacuo}$ to produce 8.1 g of a crude mixture. β-L-4'-benzyl-2'-deoxy-3'-oxacytidine and its α-L isomer were formed in a ratio of 5:1 respectively. This crude mixture was separated by chromatography on silica-gel (5% methanol in ethylacetate) to generate the pure β-L (β) isomer (4.48 g). Alternatively, recrystallization of the mixture from ethanol produces 4.92 g of pure β isomer and 3.18 g of a mixture of β and α-isomers in a ratio of 1:1.

EXAMPLE 16

2-(S)-Benzoyloxymethyl-1,3-dioxolan-4-(S)-yl)-2-oxo-4-amino-pyrimidine (Compound 16).

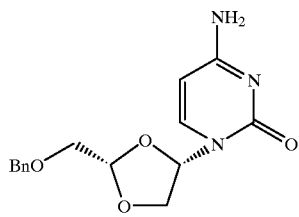

Compound 16

The protected β-L isomer (4.4 g) (Compound 15) was suspended in saturated methanolic ammonia (250 mL) and stirred at room temperature for 18 hours in a closed vessel. The solvents were then removed $_{in\text{-}vacuo}$ to afford the deacetylated nucleoside in pure form.

EXAMPLE 17

2-(S)-hydroxymethyl-1,3-dioxolan-4-(S)-yl)-2-oxo-4-amino-pyrimidine (Compound 17)

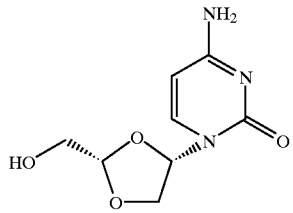

Compound 17

β-L-4'-Benzyl-2'-deoxy-3'-oxacytidine (Compound 16) was dissolved in EtOH (200 mL) followed by addition of cyclohexene (6 mL) and palladium oxide (0.8 g). The reaction mixture was refluxed for 7 hours then it was cooled and filtered to remove solids. The solvents were removed from the filtrate by vacuum distillation. The crude product was purified by flash chromatography on silica-gel (5% MeOH in EtOAc) to yield a white solid (2.33 g; 86% overall yield). $\alpha_D^{22}$=−46.7° (c=0.285; MeOH) m.p.=192–194° C.

The following examples 18–20 illustrate a method of preparing the starting material of example 1 (2-(S)-benzoyloxymethyl-4-carboxylic acid-1,3-dioxolane methyl ester).

EXAMPLE 18

Preparation of D-glyceric acid (Compound 18)

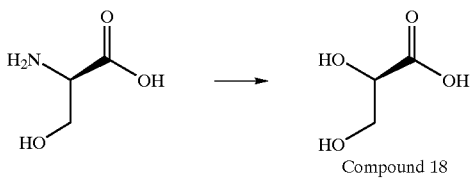

Compound 18

Portions of sulfuric acid (297 mL; 11.14 mol; 1.23 eq) was added to a large excess of water (7,300 mL) under stirring and cooling (0–5° C.). D-Serine (952 g;9.06 mol;1 eq) was added in one portion under vigorous stirring, followed by dropwise addition of aqueous sodium nitrite (769 g;11.14 mol; 1.23 eq in 3,060 mL water). Temperature was kept between 0–5° C. during the addition time (seven hours). The reaction vessel was stirred overnight at room temperature and the reaction monitored by TLC (ninhydrin). In order to complete the reaction, additional sulfuric acid (115 mL; 4.31 mol; 0.47 eq) and aqueous sodium nitrite (255 g; 3.69 mol; 0.4 eq in 1,100 mL water) was added, keeping the reaction vessel temperature between 0–5° C. The reaction vessel was then kept under stirring at room temperature for another 18 hours. Nitrogen was bubbled through the solution for one hour and the water removed by vacuum, keeping the reaction vessel temperature between 28–30° C. The residue (D-glyceric acid) was co-evaporated with toluene (3×1L)

EXAMPLE 19

Preparation of D-methyl glycerate (Compound 19)

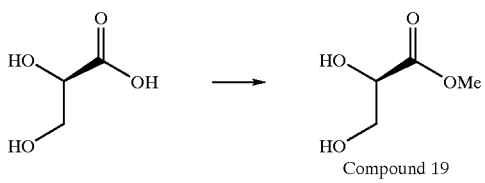

Compound 19

D-glyceric acid was stirred with methanol (6L) for 30 minutes and the solid removed by filtration. The clear solution was stirred at room temperature for 35–38 hours and the reaction monitored by TLC (DCM/MeOH 8:2 Rf=0.63). Methanol was removed by vacuum to yield a yellow viscous syrup (1,100 g).

EXAMPLE 20

Preparation of 2-(R,S)-benzoyloxymethyl-4-R-methylcarboxylate-1,3-dioxolane (Compound 20)

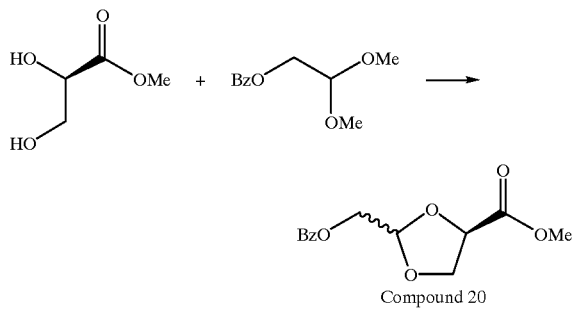

Compound 20

A mixture of benzoyloxyacetaldehyde dimethyl acetal (146 g, 95%, 0.66 mole, 1 eq) and D-methyl glycerate (99 g, 0.82 mole, 1.25 eq) was heated to 90° C., followed by the addition of solid PTSA (2.75 g, 0.145 moles, 0.022 eq). The reaction mixture was kept under vacuum (water aspirator) at 90–95° C. for 2.5 hours (TLC, Hexanes/Ethylacetate 1:1, Rf-0.47). The reaction mixture was cooled down to room temperature, diluted with ethylacetate (250 mL) and poured onto saturated NaHCO3 solution (250 mL) under stirring. The organic phase was separated and the aqueous phase was extracted one with ethylacetate (150 mL). The combined organic phase was concentrated and purified on a silica gel column eluting with 5–10% ethylacetate/hexanes to yield 112.4 g of the desired product as a light yellow oil (59%) with β/α ratio of 2.1:1. The β-anomer of compound 20 can be then separated from the α-anomer of compound 20 according to Examples 1–3, 4–5, 6–7, 8–9, 10–11, or 12–13.

EXAMPLE 21

Preparation of β 2-(R)-benzoyloxymethyl-1,3-dioxolane-4-(R)-carboxylic acid (Compound 21)

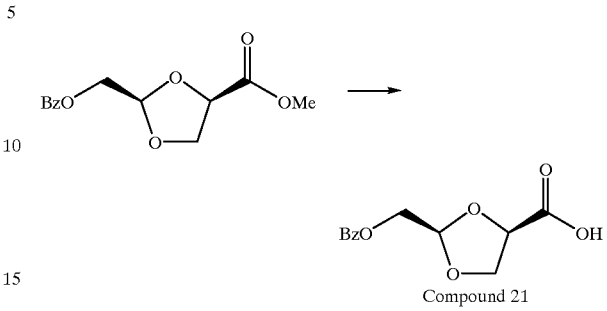

Compound 21

β 2-(R)-benzoyloxymethyl-1,3-dioxolane-4-(R)-methylcarboxylate-1,3-dioxolane (15.327 g; 57.57 mmol) is dissolved in THF (60 mL) then water (15 mL) was added under stirring. The internal temperature was set to 20° C. Then, a solution of LIOH (2.41 g; 57.57 mmol) in water (15 mL) was added dropwise over 7 minutes. The reaction mixture was stirred at 22° C. for an additional 40 minutes. THF was removed under vacuum, and the residue diluted with water (70 mL). The resulting solution was extracted with dichloromethane (2×35 mL). The aqueous phase was acidified by 30% $H_2SO_4$ (9.5 mL) under tight pH-meter control (initial pH:8.36 to 3.02) then extracted with DCM (4×60 mL). The organic phases were combined and the solvent removed under vacuum to furnish a light green syrup (14.26 g) which was kept under vacuum overnight.

EXAMPLE 22

Preparation of β 2-(R)-benzoyloxymethyl-4-(R,S)-methylcarboxylate-1,3-dioxolane (Compound 22).

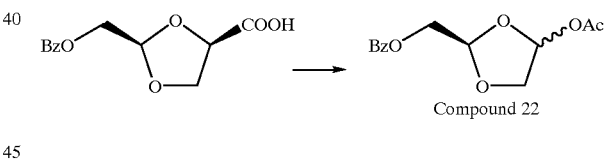

Compound 22

Lead tetraacetate (944, 8 g; 2,024 mole; 1,2 eq) was added portion-wise to an acetonitrile (6.8 L) solution of the acid (425,5 g; 1,687 mole; 1,0 eq) and pyridine (193 mL) in an ice bath. The reaction vessel was allowed to warm up to room temperature and stirred. The reaction was checked by TLC (hexanes:ethyl acetate 6:4). It was filtered through a small pad of celite (about 1 inch). Then, the filtrate was poured onto 5 L of saturated aqueous sodium bicarbonate solution (reaction mixture turned brown), and the pH as adjusted to 8 by adding solid sodium bicarbonate. The filtrate was again filtered through a small pad of celite (about 1 inch) to remove the black lead salts to yield a pale yellow mixture. The organic phase was separated and the aqueous phase was extracted with ethylacetate (4×2L). The combined organic phase was concentrated, and the oil obtained was co-evaporated with toluene (3×2L) to yield a brown syrup.

This syrup (374 g) was further purified by filtering through a small pad of silica gel (1 g crude; 2 g silica), eluting with 3.5 L of the solvent mixture (ethyl acetate:hexanes 8:2) to yield 332,3 g (74%) of pure product. This last filtration step is optional.

EXAMPLE 23

Preparation of 9-(2-(R)-benzoyloxymethyl-1,3-dioxolan-4-yl)-6-chloro-2-amino purine (Compound 23a) and 9-(2-(R)-benzoyloxymethyl-1,3-dioxolan-4-yl)-6-iodo-2-amino purine (Compound 23b)

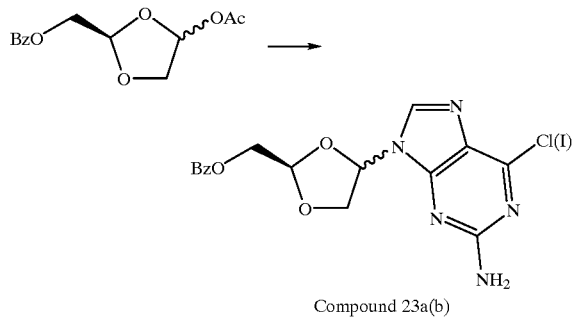

Compound 23a(b)

TMSI (28.2 mL; 198.12 mol eq) was added dropwise to a dichloromethane (750 mL) solution of the sugar (2-(R)-benzoyloxymethyl-4-carboxyl-1,3-dioxolane) (52.75 g; 198.12 mmol; 1 eq) at 15° C. After 2.5 hr at 15° C., silylated 2-amino-6-chloropurine (62 g; 198 mmol; 1 eq) was added to the reaction mixture as a solid. The stirring was continued at the same temperature for another 2.5 hr. The reaction mixture was allowed to warm up slowly to room temperature followed by continued stirring for 40 hr at room temperature. Then, the mixture was poured onto aq NaHCO₃ solution (1 L). It was stirred for 20 min with Na₂S₂O₃ and filtered through a small pad celite. Then, the organic phase was separated and the aqueous phase was extracted with dichloromethane (1×200 mL). The combined organic phases were concentrated to get 87 g of the crude. Column purification of the crude on silica gel (450 g), eluting with ethylacetate/hexane (6:4) yielded 67.7 g (81%; 1:1 chloro/iodo mixture) of the coupled product with β/α ratio 2.3:1.

Alternatively, if the desired final product is the same compound but with opposite stereochemistry (i.e. a 2:1 mixture of β:α stereoisomers in the L-configuration). The procedure discussed above is followed. However, the sugar 2-(R)-benzoyloxymethyl-4-carboxyl-1,3-dioxolane is replaced with 2-(S)-benzoyloxymethyl-4-carboxyl-1,3-dioxolane.

EXAMPLE 24

Preparation of 9-(2-(R)-benzoyloxymethyl-1,3-dioxolan-4-yl)-6-(N-cyclopropyl)amino-2-amino purine (Compound 24).

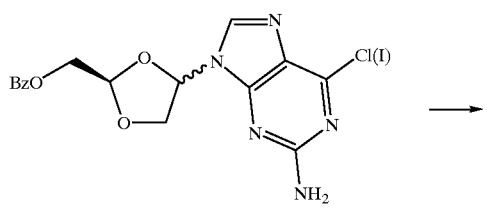

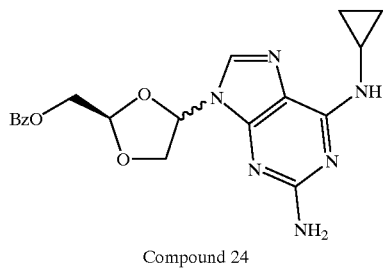

Compound 24

A solution of the starting material (Compound 23: 6.3 g; 14.95 mmol; 1 eq; average F.W.=421.52; Cl:I/1:1) in ethanol (100 mL) was refluxed at 75–80° C. with cyclopropylamine (3.1 mL; 44.84 mmol; 3 eq) for 20 hrs and cooled to room temperature. The reaction mixture was concentrated, dissolved in dichloromethane (25 mL) and poured onto saturated aqueous sodium bicarbonate solution. After 10 min. of stirring, the organic phase was separated, and the aqueous phase was extracted with dichloromethane (2×15 mL). Then, the combined organic phase was concentrated to get a quantitative yield of the crude, which was then purified by column chromatography (silica gel, ethylacetate:MeOH 98.5:2.5 and 95:5) to yield 5.3 g (89%) of the product as a β/α mixture.

EXAMPLE 25

Preparation of 9-(2-(R)-hydroxymethyl-1,3-dioxolan-4-yl)-6-(N-cyclopropyl)amino-2-amino purine (Compound 25)

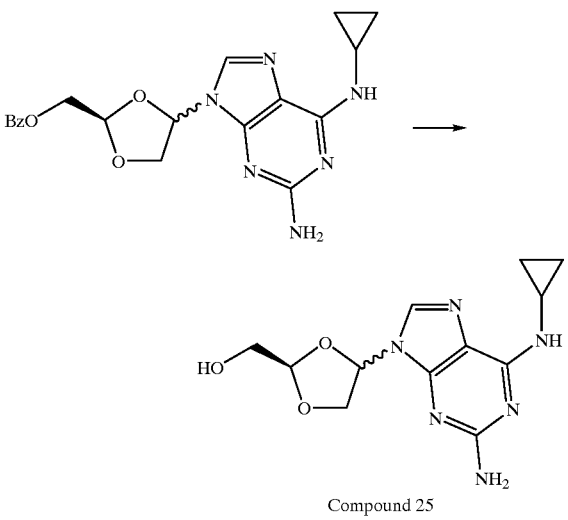

Compound 25

The starting material (Compound 24: 3.3 g) was stirred with ammonia in MeOH (80 mL; 2M) for 20 hrs. Nitrogen was bubbled through the reaction mixture to remove the excess ammonia. Then, the solution was concentrated to yield the crude as a β/α mixture (β/α=2.3:1). The β/α isomers were separated by chromatography on silica gel using DCM/MeOH as eluent to yield 1.18 g (70% β isomer).

EXAMPLE 26

Preparation of 9-(2-(R)-hydroxymethyl-1,3-dioxolan-4-yl-6-(N-2-cyclopropyl-2-aminomethoxyl)-2-amino purine (Compound 26)

Compound 26

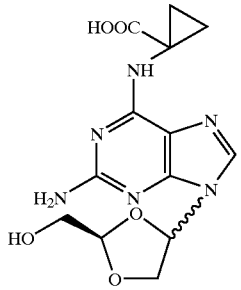

A solution of (2R)-2-benzoyloxymethyl-4-(2'-amino-6'-cyclopropylamino-purine-9'-yl)-1,3-dioxolane (480 mg) in 30 ml of saturated methanolic ammonia was stirred at room temperature for 18 h. The mixture was evaporated to dryness in vacuo. The residue was dissolved in 20 ml of water, washed twice with 10 ml of methylene chloride and lyophilized to give 283 mg of white solid in 80% yield. The resulting product had a mixture of β:α anomers having a ratio of about 2:1.

Alternatively, if the desired final product is the same compound but with opposite stereochemistry (i.e. a 2:1 mixture of β:α stereoisomers in the L-configuration). The procedure discussed above is followed. However, when following the steps of Example 23, the sugar 2-(R)-benzoyloxymethyl-4-carboxyl-1,3-dioxolane is replaced with 2-(S)-benzoyloxymethyl-4-carboxyl-1,3-dioxolane.

EXAMPLE 27

Preparation of 9-(2-(S)-hydroxymethyl-1,3-dioxolan-4-yl)-2-amino purine (Compound 27)

Compound 27

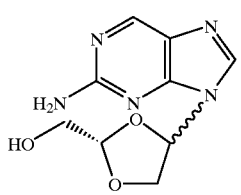

The procedure of Example 23 was performed. Thereafter 6.3 g of Compound 23 was subject to hydrogenation conditions under 50 psi of hydrogen over 10% Pd/c in 300 mL of ethanol containing 100 mL of triethylamine. After 3 hours of shaking, the catalyst was removed by filtration. Then the solvent was evaporated to yield a solid which was recrystallised to from ethanol-ether to give about 4 g of Compound 27 having about a 2:1 mixture of β:α stereoisomers in the L-configuration.

Alternatively, if the desired final product is the same compound but with opposite stereochemistry (i.e. about a 2:1 mixture of β:α stereoisomers in the D-configuration). The procedure discussed above is followed. However, when following the steps of Example 23, the sugar 2-(S)-benzoyloxymethyl-4-carboxyl-1,3-dioxolane is replaced with 2-(R)-benzoyloxymethyl-4-carboxyl-1,3-dioxolane.

EXAMPLE 28

Preparation of 9-(2-(S) hydroxymethyl-1,3-dioxolan-4-yl)-6-amino purine (Compound 28)

Compound 28

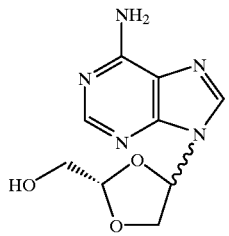

The procedures set forth in Examples 23 and 24 were performed. However when following the steps of Example 23, the 1 equivalent of the silated 2-amino-6-chloropurine is replaced with 1 equivalent of silated 6-aminopurine. The result is a yield of 9-(2-(S)-hydroxymethyl-1,3-dioxolan-4-yl)-6-amino purine having a β:α ratio of about 2:1.

Alternatively, if the desired final product is the same compound but with opposite stereochemistry (i.e. a 2:1 mixture of β:α stereoisomers in the D-configuration). The procedure discussed above is followed. However, when following the steps of Example 23, the sugar 2-(S)-benzoyloxymethyl-4-carboxyl-1,3-dioxolane is replaced with 2-(R)-benzoyloxymethyl-4-carboxyl-1,3-dioxolane.

EXAMPLE 29

Preparation of 9-(2-(S) hydroxymethyl-1,3-dioxolan-4-yl)-6,2-diamino purine (Compound 29)

Compound 29

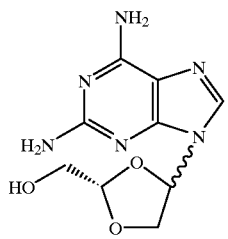

The procedure of Example 23 was performed. Thereafter, 6 g of Compound 23 was dissolved in 0.9 L of methanol saturated at 0° C. with dry ammonia and the solution is heated in a steel bomb to 105° C. to 110° C. for 16 hours. The solution was evaporated to dryness and the residue purified by chromatography on silica gel using chloroform-methanol (4:1) as the eluent to give about 3 g of crude Compound 29. The product can be recrystallised from methanol-ether to yield purified Compound 29 having a β:α ratio of about 2:1.

Alternatively, if the desired final product is the same compound but with opposite stereochemistry (i.e. a 2:1 mixture of β:α stereoisomers in the D-configuration). The procedure discussed above is followed. However, when following the steps of Example 23, the sugar 2-(S)-benzoyloxymethyl-4-carboxyl-1,3-dioxolane is replaced with 2-(R)-benzoyloxymethyl-4-carboxyl-1,3-dioxolane.

EXAMPLE 30

Preparation of 9-(2-(S) hydroxymethyl-1,3-dioxolan-4-yl)-6-oxo-2-amino purine (Compound 30)

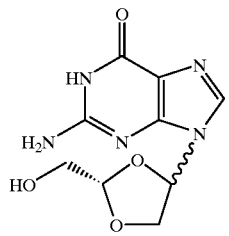

Compound 30

The procedure of Example 23 was performed. Thereafter, about 6 g of Compound 23 was dissolved in a mixture of 200 mL of methanol, 50 mL of water and 10 g of NaoH. The solution was heated under reflux for 5 hours after which time it was diluted with 300 mL of water and excess pyridinium sulfonate resin. The slurry was filtered, the resin washed with water and the combined aqueous filtrates were evaporated to dryness in vacuo to leave a residue which was taken up in 50% aqueous methanol. The solution was treated with activated charcoal, filtered and the filtrate evaporated to dryness in vacuo to give a solic residue that was recrystalized from ethanol water to yield pure compound 30 having a β:α ratio of about 2:1.

Alternatively, if the desired final product is the same compound but with opposite stereochemistry (i.e. a 2:1 mixture of β:α stereoisomers in the D-configuration). The procedure discussed above is followed. However, when following the steps of Example 23, the sugar 2-(S)-benzoyloxymethyl-4-carboxyl-1,3-dioxolane is replaced with 2-(R)-benzoyloxymethyl-4-carboxyl-1,3-dioxolane.

EXAMPLE 31

Preparation of 9-(2-(S) hydroxymethyl-1,3-dioxolan-4-yl)-2-oxo-4-amino-5-methyl pyrimidine (Compound 31)

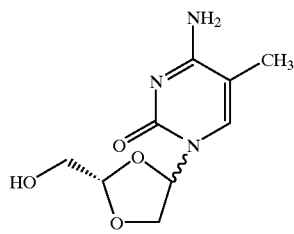

Compound 31

The procedure of Example 23 was performed followed by the procedure of Example 25. However, when following the steps of Example 23, the 1 equivalent of the silated 2-amino-6-chloropurine is replaced with 1 equivalent of silated 2-oxo-4-amino-5-methyl-pyrimidine. The result is a yield of 9-(2-(S)-hydroxymethyl-1,3-dioxolan-4-yl)-2-oxo-4-amino-5-methyl pyrimidine having a β:α ratio of about 2:1.

Alternatively, if the desired final product is the same compound but with opposite stereochemistry (i.e. a 2:1 mixture of β:α stereoisomers in the D-configuration). The procedure discussed above is followed. However, when following the steps of Example 23, the sugar 2-(S)-benzoyloxymethyl-4-carboxyl-1,3-dioxolane is replaced with 2-(R)-benzoyloxymethyl-4-carboxyl-1,3-dioxolane.

EXAMPLE 32

Preparation of 9-(2-(S) hydroxymethyl-1,3-dioxolan-4-yl)-2-oxo-4-amino-5-fluoro pyrimidine (Compound 32)

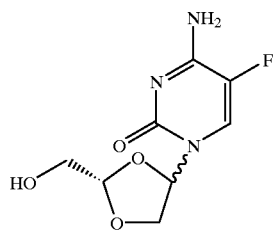

Compound 32

The procedure of Example 23 was performed followed by the procedure of Example 25. However, when following the steps of Example 23, the 1 equivalent of the silated 2-amino-6-chloropurine is replaced with 1 equivalent of silated 2-oxo-4-amino-5-fluoro-pyrimidine. The result is a yield of 9-(2-(S) hydroxymethyl-1,3-dioxolan-4-yl)-2-oxo-4-amino-5-fluoro pyrimidine having a β:α ratio of about 2:1.

Alternatively, if the desired final product is the same compound but with opposite stereochemistry (i.e. a 2:1 mixture of β:α stereoisomers in the D-configuration). The procedure discussed above is followed. However, when following the steps of Example 23, the sugar 2-(S)-benzoyloxymethyl-4-carboxyl-1,3-dioxolane is replaced with 2-(R)-benzoyloxymethyl-4-carboxyl-1,3-dioxolane.

EXAMPLE 33

Preparation of 9-(2-(S) hydroxymethyl-1,3-dioxolan-4-yl)-2,4-dioxo pyrimidine (Compound 33)

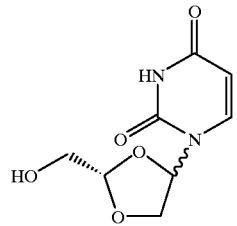

Compound 33

The procedure of Example 23 was performed followed by the procedure of Example 25. However, when following the steps of Example 23, the 1 equivalent of the silated 2-amino-6-chloropurine is replaced with 1 equivalent of silated 2,4-dioxo pyrimidine. The result is a yield of 9-(2-(S)-hydroxymethyl-1,3-dioxolan-4-yl)-2,4-dioxo pyrimidine having a β:α ratio of about 2:1.

Alternatively, if the desired final product is the same compound but with opposite stereochemistry (i.e. a 2:1 mixture of β:α stereoisomers in the D-configuration. The above formula is followed. However, when following the steps of Example 23, the sugar 2-(S)-benzoyloxymethyl-4- carboxyl-1,3-dioxolane is replaced with 2-(R)-benzoyloxymethyl-4-carboxyl-1,3-dioxolane.

EXAMPLE 34

Preparation of 9-(2-(S) hydroxymethyl-1,3-dioxolan-4-yl)-2,4-dioxo-5-methyl pyrimidine (Compound 34)

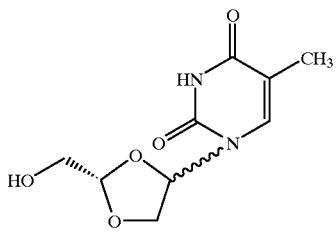

Compound 34

The procedure of Example 23 was performed followed by the procedure of Example 25. However, when following the steps of Example 23, the 1 equivalent of the silated 2-amino-6-chloropurine is replaced with 1 equivalent of silated 2,4-dioxo-5-methyl pyrimidine. The result is a yield of 9-(2-(S) hydroxymethyl-1,3-dioxolan-4-yl)-2,4-dioxo-5-methyl pyrimidine having a β:α ratio of about 2:1.

Alternatively, if the desired final product is the same compound but with opposite stereochemistry (i.e. a 2:1 mixture of β:α stereoisomers in the D-configuration). The procedure discussed above is followed. However, when following the steps of Example 23, the sugar 2-(S)-benzoyloxymethyl-4-carboxyl-1,3-dioxolane is replaced with 2-(R)-benzoyloxymethyl-4-carboxyl-1,3-dioxolane.

Some modifications and variations of the present invention including but not limited to selection of enzymes with high degree of sequence homology and optimization of reaction conditions will be obvious to a person of ordinary skill in the art from the foregoing detailed description of the invention. Such modifications and variations are intended to fall within the scope of one or more embodiments of the present invention as defined by the following claims.

What is claimed is:

1. A process for stereoselectively producing a dioxolane nucleoside analogue from an anomeric mixture of β and α anomers represented by the following formula A or formula B:

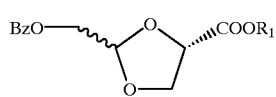
(A)

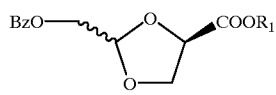
(B)

wherein $R_1$ is selected from the group consisting of $C_{1-6}$ alkyl and $C_{6-15}$ aryl, and Bz is benzoyl, the process comprising:

stereoselectively hydrolyzing said mixture with an enzyme selected from the group consisting of Protease N (Bacillus subtilus protease), Alcalase® (Subtilisin Carlsberg protease), Savinase® (Bacillus lentus subtilisin protease), ChiroCLEC-BL (Bacillus lichenifor- mis Subtilisin protease), PS-30 (Pseudomonas cepacia lipase), and ChiroCLEC-PC (Pseudomonas cepacia lipase) to stereoselectively hydrolyze predominantly one anomer to form a product wherein $R_1$ is replaced with H;

separating the product from unhydrolyzed starting material to produce a second mixture;

stereoselectively replacing the functional group at the C4 position with a purinyl or pyrimidinyl or derivative thereof by reacting said second mixture with a purine or pyrimidine base or derivative thereof.

2. The process of claim 1, wherein the step of hydrolyzing results in the starting material having an anomeric purity of at least 97%.

3. The process of claim 1, wherein the step of hydrolyzing results in the starting material having an anomeric purity of at least 98%.

4. The process of claim 1, wherein the step of hydrolyzing results in the starting material having an anomeric purity of at least 98.5%.

5. The process of claim 1, wherein the step of hydrolyzing results in the starting material having an anomeric purity of at least 98.8%.

6. The process of claim 1, wherein the step of hydrolyzing results in the product having an anomeric purity of at least 97%.

7. The process of claim 1, wherein the step of hydrolyzing results in the product having an anomeric purity of at least 98%.

8. The process of claim 1, wherein the step of hydrolyzing results in the product having an anomeric purity of at least 98.5%.

9. The process of claim 1, wherein the step of hydrolyzing results in the product having an anomeric purity of at least 98.8%.

10. The process of claim 1, wherein the purine or pyrimidine base or derivative thereof is selected from the group consisting of:

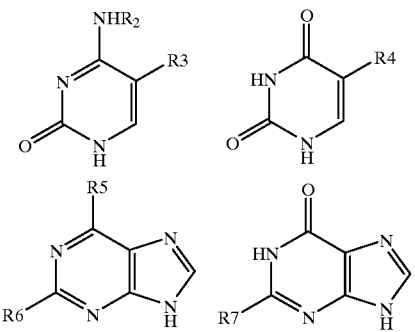

wherein $R_2$ is selected from the group consisting of hydrogen, $C_{1-6}$ alkyl, $C_{1-6}$ acyl and $R_8C(O)$ wherein $R_8$ is hydrogen or $C_{1-6}$ alkyl;

$R_3$ and $R_4$ are each independently selected from the group consisting of hydrogen, $C_{1-6}$ alkyl, bromine, chlorine, fluorine, iodine and $CF_3$; and $R_5$, $R_6$ and $R_7$ are each independently selected from the group consisting of hydrogen, bromine, chlorine, fluorine, iodine, amino, hydroxyl and $C_{3-6}$ cycloalkylamino.

11. The process of claim 1, wherein the purine or pyrimidine base or derivative thereof is selected from the group consisting of:

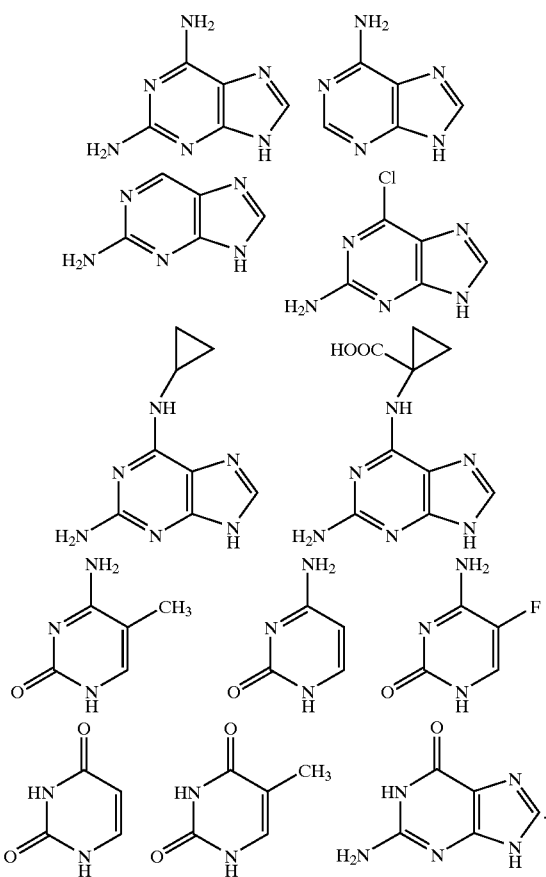

12. The process of claim 1, wherein the step of replacing further comprises:

acylating the second mixture to produce an acylated second mixture; and

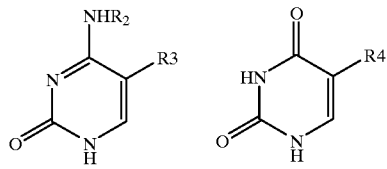

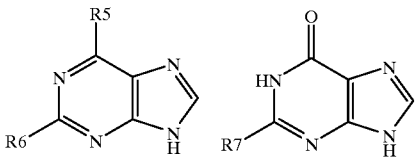

glycosylating the acetylated second mixture with said a purine or pyrimidine base or derivative thereof and a Lewis Acid to produce the dioxolane nucleoside analogue.

13. A process according to claim 1, wherein the step of stereoselectively replacing the functional group at the C4 position ($COOR_1$) involves reacting the second mixture with a base selected from the group consisting of:

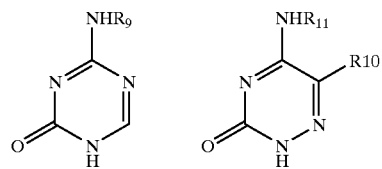

wherein $R_9$ and $R_{11}$ are each, independently, selected from the group consisting of hydrogen, $C_{1-6}$ alkyl, $C_{1-6}$ acyl and $R_8C(O)$, $R_8$ is hydrogen or $C_{1-6}$ alkyl, and $R_{10}$ is selected from the group consisting of hydrogen, $C_{1-6}$ alkyl, bromine, chlorine, fluorine, iodine and $CF_3$.

14. A process according to claim 10, wherein the step of hydrolyzing results in the starting material having an anomeric purity of at least 97%.

15. A process according to claim 10, wherein the step of hydrolyzing results in the product having an anomeric purity of at least 97%.

16. A process according to claim 11, wherein the step of hydrolyzing results in the starting material having an anomeric purity of at least 97%.

17. A process according to claim 11, wherein the step of hydrolyzing results in the product having an anomeric purity of at least 97%.

18. A process according to claim 13, wherein the step of hydrolyzing results in the starting material having an anomeric purity of at least 97%.

19. A process according to claim 13, wherein the step of hydrolyzing results in the product having an anomeric purity of at least 97%.

* * * * *

UNITED STATES PATENT AND TRADEMARK OFFICE
CERTIFICATE OF CORRECTION

PATENT NO.        : 6,541,625 B2                              Page 1 of 1
APPLICATION NO. : 09/779853
DATED              : April 1, 2003
INVENTOR(S)      : Alex Cimpoia It is certified that error appears in the above-identified patent and that said Letters Patent is hereby corrected as shown below:

Column 32, line 42, Claim 10 reads "NHR2" should read --NHR$_2$--
Column 32, line 43, Claim 10 reads "R3" should read --R$_3$--
Column 32, line 43, Claim 10 reads "R4" should read --R$_4$--
Column 32, line 47, Claim 10 reads "R5" should read --R$_5$--
Column 32, line 53, Claim 10 reads "R6" should read --R$_6$--
Column 32, line 53, Claim 10 reads "R7" should read --R$_7$--
Column 33, lines 41-48, to Column 34, lines 1-9, Claim 10 read,

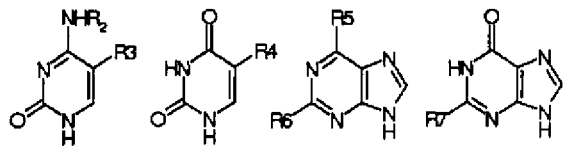

should read

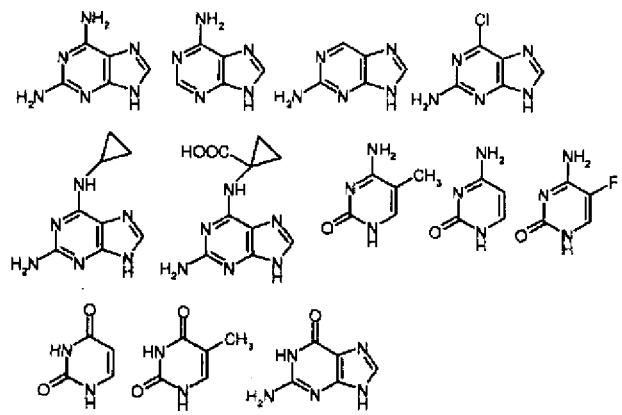

Column 34, line 10, Claim 12 reads "with said a" should read --with said--
Column 34, line 20, Claim 13 reads "R10" should read --R$_{10}$--

Signed and Sealed this

Seventh Day of September, 2010

David J. Kappos
*Director of the United States Patent and Trademark Office*